(12) United States Patent
Moro

(10) Patent No.: US 12,318,231 B2
(45) Date of Patent: Jun. 3, 2025

(54) NEEDLE DISPOSAL CONTAINER

(71) Applicant: NITTA MOLD CORPORATION, Koka (JP)

(72) Inventor: Takumi Moro, Konan (JP)

(73) Assignee: NITTA MOLD CORPORATION, Koka (JP)

( * ) Notice: Subject to any disclaimer, the term of this patent is extended or adjusted under 35 U.S.C. 154(b) by 63 days.

(21) Appl. No.: 18/367,745

(22) Filed: Sep. 13, 2023

(65) Prior Publication Data
US 2025/0082426 A1    Mar. 13, 2025

(51) Int. Cl.
*A61B 50/36*    (2016.01)

(52) U.S. Cl.
CPC ................. *A61B 50/362* (2016.02)

(58) Field of Classification Search
CPC ... A61B 50/36; A61B 50/3001; A61B 50/362; A61B 17/06161; A61B 2050/0051; A61B 2050/0058; A61B 2050/364; A61M 5/3205; A61M 5/002; A61M 5/3278; B09B 3/0075; B09B 3/00; B65D 25/14
USPC .............. 206/366, 365, 571, 364, 370, 438; 220/908; 604/110
See application file for complete search history.

(56) References Cited

U.S. PATENT DOCUMENTS

| 5,415,315 A * | 5/1995 | Ramirez | A61B 50/362 220/345.2 |
| 2003/0038046 A1* | 2/2003 | Panek, Jr. | A61M 5/3205 206/366 |
| 2003/0183546 A1* | 10/2003 | Crawford | A61B 50/362 206/370 |
| 2017/0209230 A1* | 7/2017 | Nakagami | A61B 50/362 |

FOREIGN PATENT DOCUMENTS

| JP | 2016-032557 A | 3/2016 |
| JP | 2019-612 A | 1/2019 |
| JP | 2022-105107 A | 7/2022 |

* cited by examiner

*Primary Examiner* — King M Chu
(74) *Attorney, Agent, or Firm* — Oliff PLC

(57) ABSTRACT

A needle disposal container includes a container body and a covering attached to the container body. The covering includes a lid body that covers the open top of the container body and a movable member movable relative to the lid body between a hold position and a retract position. The lid body has a first wall having a first surface, and the movable member has a second wall having a second surface. The first and second surfaces together form a cylindrical surface that defines an insertion opening. The cylindrical surface has a first rotation-preventer that prevents rotation of a first needle unit inserted into the insertion opening and a second rotation-preventer that prevents rotation of a second needle unit inserted into the insertion opening. The second needle unit has a second needle hub with a smaller diameter than a diameter of a first needle hub of the first needle unit.

12 Claims, 11 Drawing Sheets

NEEDLE DISPOSAL CONTAINER

FIELD OF THE INVENTION

The present invention relates to a needle disposal container for disposing of needle units of injectors.

BACKGROUND

There has been provided a needle disposal container that allows a user to remove a syringe needle from a syringe and disposing the same into the container without touching the needle, preventing the user from accidentally being stung with the needle. For example, a needle disposal container disclosed in JP2016-32557 includes a container body for storing a syringe needle and a lid that covers an upper opening of the container body.

The needle disposal container also includes a moving member that is slide-movable relative to the lid between a holding position and a retract position. The lid is formed with a first holding part having a concave inner surface in a substantially semi-arc shape, and the moving member is formed with a second holding part having a concave inner surface in a substantially semi-arc shape. When the moving member is placed at the holding position, then the concave inner surfaces of the first and second holding parts together define a dropping opening. Also, the concave inner surfaces of the first and second holding parts are formed with a plurality of engaging protrusions that protrude radially inward of the dropping opening.

One type of syringe includes a syringe body for storing an injection and a needle unit (syringe needle) attached to a tip end of the syringe body. The needle unit includes a needle hub (needle holder) and a needle supported by the needle hub. The hub has an outer peripheral surface formed with a plurality of recesses corresponding to the protrusions formed on the first and second holding parts of the needle disposal container.

In order to remove this type of needle unit (syringe needle) from the syringe body, first the moving member is placed at the holding position. Then, the needle hub is inserted into the dropping opening. As a result, the plurality of protrusions on the first and second holding parts are inserted into the recesses of the needle unit, preventing rotation of the needle hub relative to the lid. When the syringe body is rotated in a predetermined detaching direction in this state, then the syringe body is rotated relative to the needle unit and thus detached from the needle hub.

Then, the moving member is moved to the retract position to widen the dropping opening, letting the needle unit drop into the container body by its own weight. In this manner, the needle unit is removed from the container body safely and discarded into the container body.

SUMMARY

In recent year, syringes (injectors) with different diameters are used. For example, when a relatively large amount of injection needs to be injected, then a syringe with a larger diameter is used, and when a relatively small amount of injection needs to be injected, then a syringe with a smaller diameter is used. The syringe with the larger diameter has a needle nub with a larger diameter, and the syringe with the smaller diameter has a needle hub with a smaller diameter.

The dropping opening of the above-described conventional needle disposal container has a uniform diameter, and the plurality of protrusions formed on the surface of the dropping opening (i.e., the surfaces of the first and second holding parts) protrude a uniform amount in a radial direction of the dropping opening throughout their entire length in an axial direction of the dropping opening. For these reasons, the conventional needle disposal container can be used for disposing of only a needle unit (syringe needle) with a particular diameter. For example, a needle unit with a larger diameter cannot be inserted into the dropping opening.

In order to solve such a problem, it is conceivable to form a plurality of dropping openings with different diameters. In this case, however, the container body and the lid need to be larger, and the configuration would be complex, increasing manufacturing costs. Moreover, every time a user disposes needle units, the user needs to decide which one of the dropping openings fits well, which would be very confusing.

In view of the foregoing, it is an object of the invention to provide a needle disposal container for disposing of needle units with different diameters.

In order to solve the above problem, a needle disposal container according to one aspect of the invention is for disposing of a first needle unit having a first need hub and a second needle unit having a second needle hub with a smaller outer diameter than the first needle hub, the needle disposal container including comprising a container body having an open top; and a covering attached to the container body, wherein: the covering includes a lid body that covers the open top of the container body and a movable member attached to the lid body so as to be movable relative to the lid body between a hold position and a retract position in a first direction; the lid body is formed with a first wall extending in a second direction perpendicular to the first direction, the first wall having a first surface with a concave-arc cross-section; the movable member is formed with a second wall extending in the second direction, the second wall having a second surface with a concave-arc cross-section, the second surface confronting the first surface of the first wall in the first direction; the first surface of the first wall and the second surface of the second wall together form a cylindrical surface that defines an insertion opening extending in the second direction, the insertion opening having a top side and a bottom side opposite to the top side in the second direction; when the movable member is moved from the hold position to the retract position, then the second wall of the movable member moves away from the first wall of the lid body to widen the insertion opening, bringing the insertion opening into a widened state; when the movable member is moved from the retract position to the hold position, then the second wall of the movable member moves toward the first wall of the lid body to narrow the insertion opening, bringing the insertion opening into a narrow state; the cylindrical surface is formed with a first rotation-preventer and a second rotation-preventer at a position closer to the bottom side of the insertion opening than the first rotation-preventer; the first rotation-preventer prevents rotation of the first needle unit inserted into the insertion opening; and the second rotation-preventer prevents rotation of the second needle unit inserted into the insertion opening.

The first rotation-preventer preferably includes at least one first protrusion that protrudes radially inward of the insertion opening from the cylindrical surface by a first amount, and the second rotation-preventer preferably includes at least one second protrusion that protrudes radially inward of the insertion opening from the cylindrical surface by a second amount greater than the first amount.

When the first needle hub is inserted into the insertion opening in the narrow state from the top side, the first protrusion is preferably inserted into one of first cutouts formed in an outer peripheral surface of the first needle hub, and when the second needle hub is inserted into the insertion opening in the narrow state from the top side, the second protrusion is preferably inserted into one of second cutouts formed in an outer peripheral surface of the second needle hub.

The first protrusion is preferably aligned with the second protrusion in the second direction. Also, a first protrusion imaginary circle coaxial with the insertion opening in the narrow state and passing through a tip end of the first protrusion preferable has a first diameter that is smaller than an outer diameter of the first needle hub and greater than a first bottom diameter of a first hub imaginary circle defined by bottom surfaces of the first cutouts, and that a second protrusion imaginary circle coaxial with the insertion opening in the narrow state and passing through a tip end of the second protrusion preferably has a second diameter that is smaller than an outer diameter of the second needle hub, greater than a second bottom diameter of a second hub imaginary circle defined by bottom surfaces of the second cutouts, and smaller than the first bottom diameter of the first hub imaginary circle. When the first needle hub is inserted into the insertion opening in the narrow state from the top side, the first needle hub preferably abuts the second protrusion.

The first protrusion is preferably formed on each of the first surface and the second surface, and the second protrusion is preferably formed on each of the first surface and the second surface in continuous with the corresponding first protrusion in the second direction.

The pair of the first protrusions are preferably formed on the first surface of the first wall with an interval in a circumferential direction of the insertion opening, and another pair of the first protrusions are preferably formed on the second surface of the second wall with an interval in the circumferential direction. Also, a pair of the second protrusions are preferably formed on the first surface of the first wall with an interval in the circumferential direction, and another pair of the second protrusions are preferably formed on the second surface of the second wall with an interval in the circumferential direction.

The cylindrical surface is preferably formed with at least one insert-regulating protrusion protruding radially inward of the insertion opening at a position closer to the bottom side of the insertion opening than the second protrusion. The second protrusion preferably abuts the first needle hub when the first needle hub is inserted into the insertion opening in the narrow state, and the insert-regulating protrusion preferably abuts the second needle hub when the second needle hub is inserted into the insertion opening in the narrow state.

According one aspect of the invention, because the first rotation-preventer and the second rotation-preventer are provided on the cylindrical surface of the insertion hole, a user can remove the first needle unit and the second needle unit from injectors and dispose the same into the container body through the same insertion hole.

BRIEF DESCRIPTION OF THE DRAWINGS

The particular features and advantages of the invention as well as other objects will become apparent from the following description taken in connection with the accompanying drawings, in which.

DETAILED DESCRIPTION

A needle disposal container according to an embodiment of the invention will be described while referring to the accompanying drawings.

The terms "front," "rear," "above" and the like will be used throughout the description assuming that the needle disposal container is disposed in an orientation in which it is intended to be used.

Figure 1:
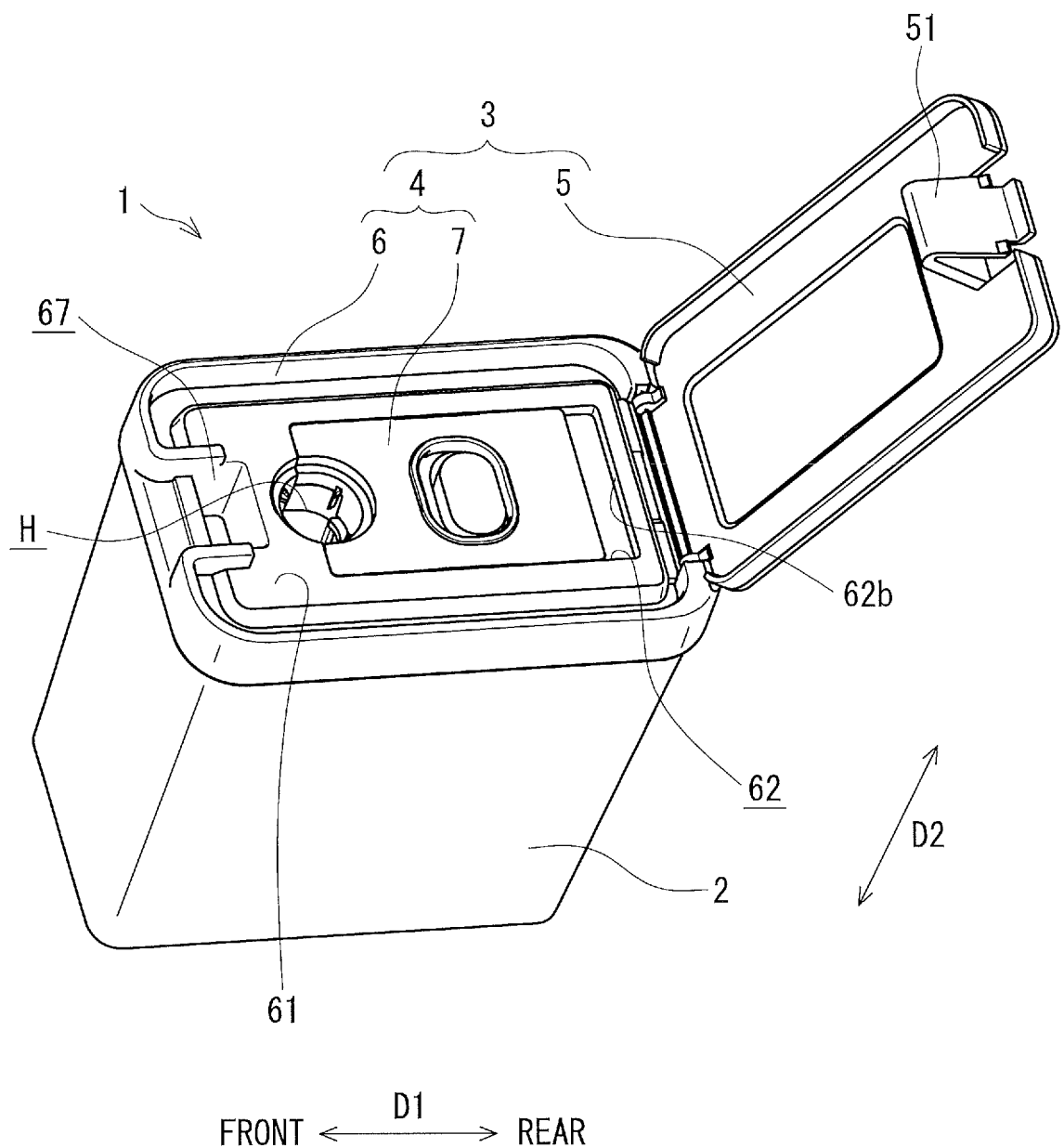
FIG. 1 is a perspective view of a needle disposal container according to an embodiment of the invention with a lid cover open.
Figure 2:
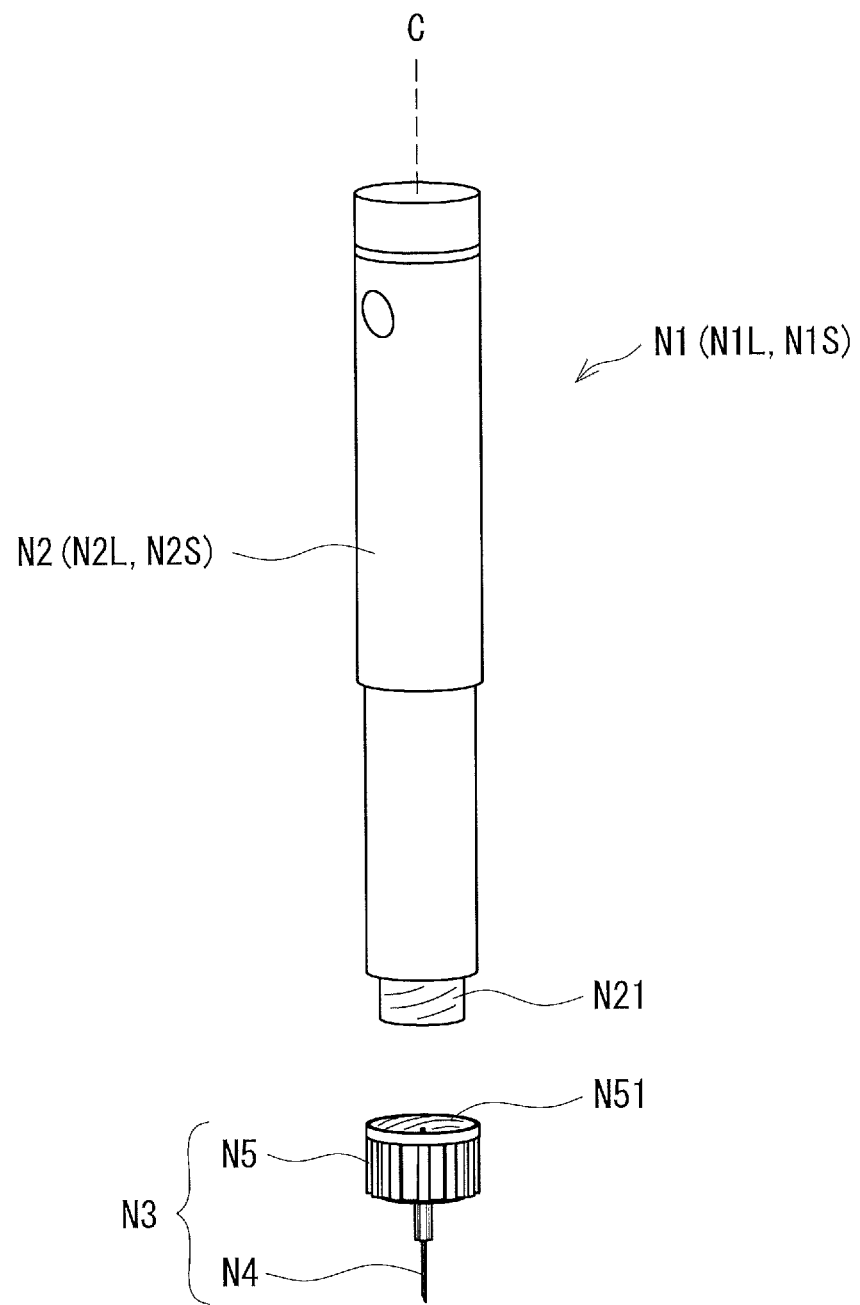
FIG. 2 is an exploded perspective view of a syringe as an example of an injector.
Figure 3:
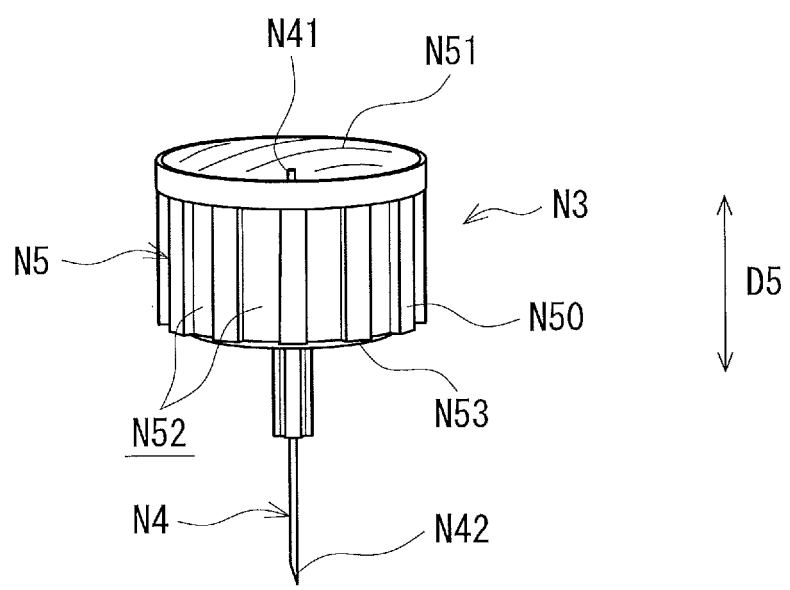
FIG. 3 is an enlarged perspective view of a needle unit of the syringe shown in FIG. 2.

With reference to FIG. 1, a needle disposal container 1 according to this embodiment includes a container body 2 and a covering 3. The container body 2 is in a box shape with an open top and a closed bottom opposite to the open top in a height direction (second direction) D2. The covering 3 is attached to the open top of the container body 2.

The needle disposal container 1 is configured to remove needle units from bodies of such injectors as syringes and to store the same. That is, the needle units are removed from the bodies of injectors and discarded into the needle disposal container 1. Here, an example of an injector including such a needle unit will be described with referring to FIGS. 2 to 4(b).

An injector N1 shown in FIGS. 2 to 4(b) is a pen-type syringe for injecting insulin into a patient's body and includes an injector main body N2 and a needle unit N3 freely detachably attached to a tip end of the injector main body N2. The injector main body N2 is formed with a male thread portion N21 at its end. The needle unit N3 includes a needle (injection needle) N4 for piercing and a needle hub N5 that holds the needle N4. The needle hub N5 is formed with a female thread portion N51 corresponding to the male thread portion N21 of the injector main body N2. The needle unit N3 is attached to the injector main body N2 by screw-fitting the male thread portion N21 of the injector main body N2 to the female thread portion N51 of the needle hub N5, and is detached from the injector main body N2 by rotating the needle unit N3 in a predetermined detaching direction about its axis C extending in a longitudinal direction D5 relative to the injector main body N2.

The needle N4 has a proximal end N41 and a distal end N42 for insertion into a patient. When the needle unit N3 is attached to the injector main body N2, then the proximal end N41 of the needle N4 pierces a seal (not shown) of a liquid medicine container (not shown) accommodated in the injector main body N2, enabling injection of liquid medicine contained in the liquid medicine container into the patient through the needle N4.

The needle hub N5 has an outer peripheral surface N50 formed with a plurality of cutouts (grooves) N52 aligned in a circumferential direction D4 with intervals. Each of the cutouts N52 extend straight along the longitudinal direction D5 of the needle N4 from a distal end N53 of the needle hub N5. That is, each cutout N52 is open at the distal end N53 (i.e, the cutout N52 has an open distal end).

There are a plurality of types of injectors N1 with different diameters. Hereinafter, the injector N1 with a relatively large diameter will be referred also to as a first injector NIL, and the injector N1 with a relatively small diameter will be referred also to as a second injector NIS, in order to differentiate therebetween.

The first injector NIL and the second injector NIS have substantially the same configuration, but differ in their diameter. Hereinafter, when components of the first injector NIL and those of the second injector NIS are distinguished, a letter "L" is added to a reference numeral for the first injector NIL, and a letter "S" is added to a reference numeral for the second injector NIS. Also, a word "first" is added to a name of a component for the first injector NIL, and a word "second" is added to a name of a component for the second injector NIS.

The first injector NIL has a larger volume and is used when a larger amount of liquid medicine needs to be injected, and the second injector NIS has a smaller volume and is used when a smaller amount of liquid medicine needs to be injected. The first needle hub N5L of the first injector NIL has a larger diameter than the second needle hub N5S of the second injector NIS. The first injector NIL and the second injector NIS may have a different length in the longitudinal direction D5.

Next, the needle disposal container 1 will be described in detail. With reference to FIG. 1, the covering 3 of the needle disposal container 1 includes a lid 4 and a lid cover 5 attached to the lid 4 so as to selectively open and close the lid 4 from the above. The lid 4 includes a lid body 6 and the movable member 7. The lid body 6 is attached to the container body 2 and covers the open top of the same. The movable member 7 is attached to the lid body 6 so as to be slidingly movable in a length direction (first direction) D1 relative to the lid body 6 between a hold position shown in FIGS. 1 and 5(a) and a retract position shown in FIG. 5(b).

Figure 9:
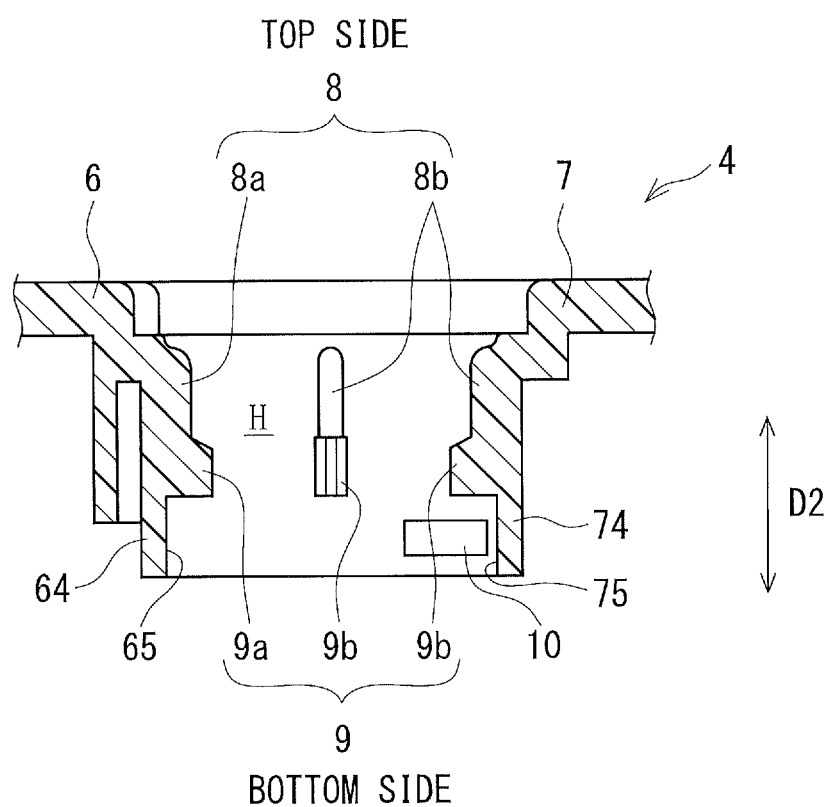
FIG. 9 is a cross-sectional view taken along a IX-IX line of FIG. 8.

The lid body 6 and the movable member 7 together define an insertion opening H extending in the height direction D2 and having a top side (upper side) and a bottom side (lower side) (FIG. 9). When the movable member 7 is moved from the hold position to the retract position, then the insertion opening His widened (i.e., the insertion opening H is set into a widened state). On the other hand, when the movable member 7 is moved from the retract position to the hold position, then the insertion opening H is narrowed (that is, the insertion opening H is set into a narrow state). In order to dispose the needle unit N3 into the needle disposal container 1, the movable member 7 is located at the hold position, and the needle unit N3 still attached to the injector main body N2 is inserted into the insertion opening H from the top side. Then, the injector main body N2 is rotated relative to the needle unit N3. After the injector main body N2 is detached from the needle unit N3, the movable member 7 is moved to the retract position so as to widen the insertion opening H. As a result, the needle unit N3 removed from the injector main body N2 drops into the container body 2 by its weight.

Figure 6:
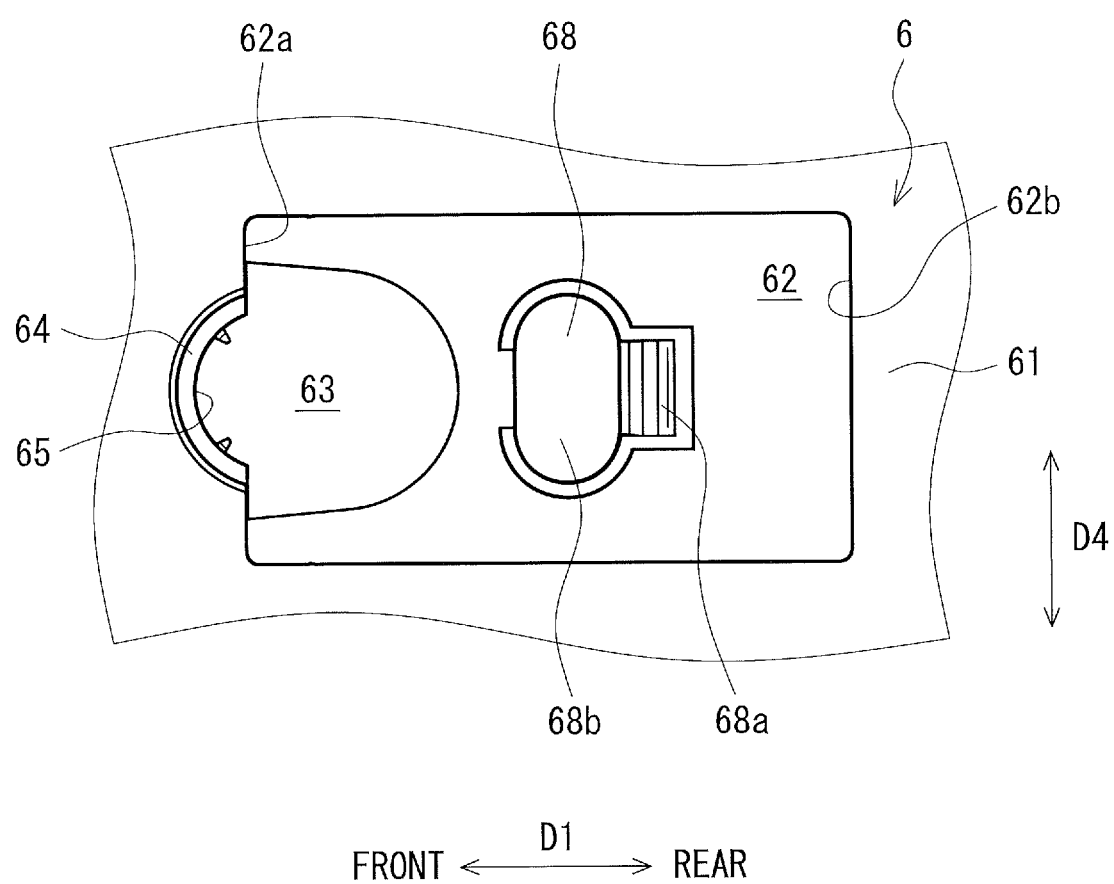
FIG. 6 is a plan view of a lid body of the lid shown in FIG. 5(a)

Components of the needle disposal container 1 will be descried in greater detail. As shown in FIGS. 1 and 6, the lid body 6 has an upper surface 61 formed with a receiving recess 62 having a front end surface 62a and a rear end surface 62b opposite to the front end surface 62a in the length direction D1. The lid body 6 is also formed with a through hole 63 penetrating the lid body 6 in the height direction D2 and a first wall 64 extending in the height direction D2. The first wall 64 is substantially in a hemicylindrical shape and has a first surface 65 extending in the height direction D2. The first surface 65 of the first wall 64 has substantially a semicircular concave shape in a cross-section and partially defines the insertion opening H.

Figure 7:
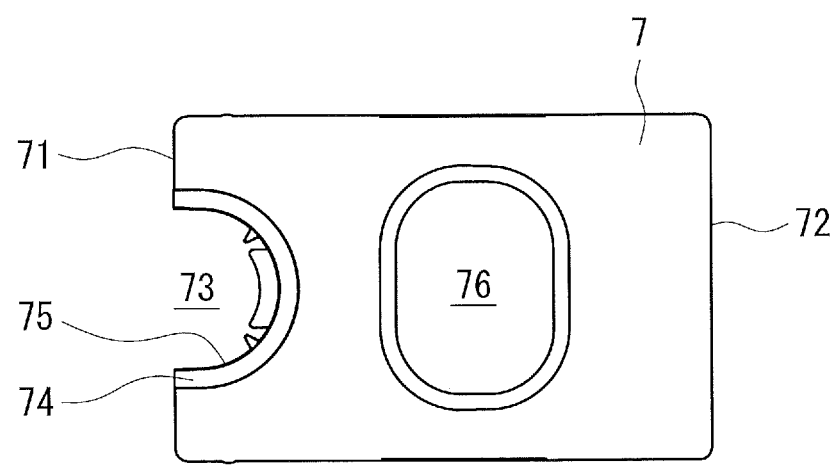
FIG. 7 is a plan view of the movable member of the lid removed from the lid body.

As shown in FIG. 7, the movable member 7 is generally in a rectangular shape in a plan view, having a front end 71 and a rear end 72 opposite to the front end 71 in the length direction D1. The movable member 7 is received in the receiving recess 62 and slidable relative to the lid body 6 in the length direction D1. When the front end 71 of the movable member 7 abuts the front end surface 62a of the receiving recess 62, the movable member 7 is located at the hold position. When the rear end 72 of the movable member 7 abuts the rear end surface 62b of the receiving recess 62, the movable member 7 is located at the retract position.

The movable member 7 is formed with a cutout 73 at the front end 71 and a second wall 74 extending in the height direction D2. The second wall 74 is substantially in a hemicylindrical shape with a second surface 75 extending in the height direction D2. The second surface 75 of the second wall 74 has substantially a semicircular concave shape in a cross-section, confronts the first surface 65 of the first wall 64 in the length direction D1, and defines the cutout 73.

Figure 5:
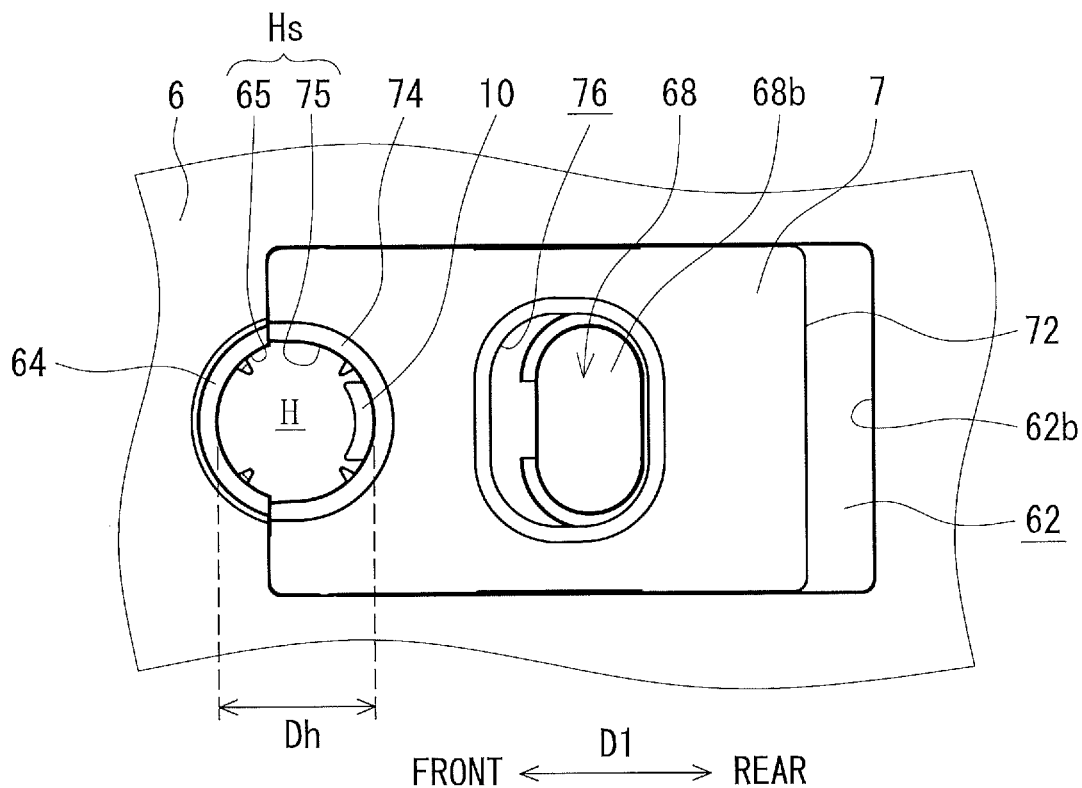
FIG. 5(a) is a plan view of a lid of the needle disposal container of FIG. 1 with a movable member at a hold position.
FIG. 5(b) is a plan view of the lid shown in FIG. 5(a) with the movable member at a retract position.
Figure 5:
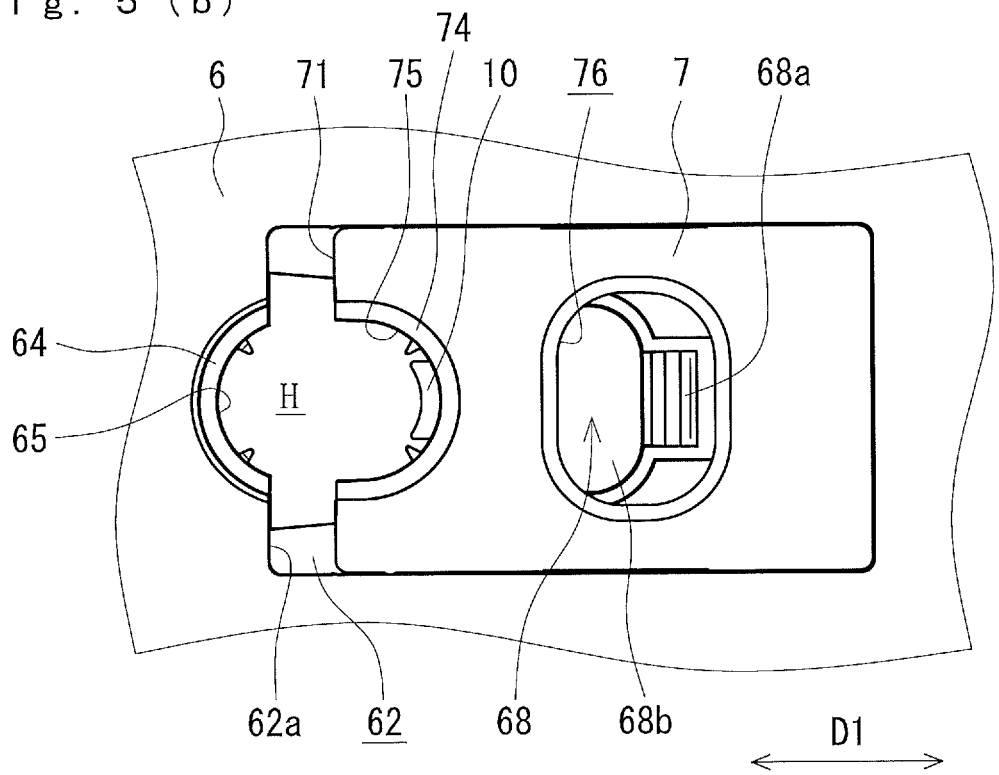

With this configuration, when the movable member 7 is located at the hold position, as shown in FIG. 5(a), the first surface 65 of the first wall 64 of the lid body 6 and the second surface 75 of the second wall 74 of the movable member 7 together form a cylindrical surface Hs that defines the insertion opening H in the narrow state. On the other hand, when the movable member 7 is at the retract position, the first surface 65 of the first wall 64 and the second surface 75 of the second wall 74 together define the insertion opening H in the widened state.

As shown in FIGS. 6 and 7, the lid body 6 is formed with a lock part 68, and the movable member 7 is formed with a window 76. The lock part 68 has an engaging part 68a and a pressing part 68b. When the movable member 7 is at the hold position, the engaging part 68a engages with an engagement part (not shown) formed on the movable member 7, thereby preventing the movable member 7 from moving relative to the lid body 6. In this condition, the pressing part 68b is exposed outside through the window 76, allowing a user to access the pressing part 68b. When the pressing part 68b is pressed downward when the movable member 7 is at the hold position, then the lock part 68 deforms downward to disengage the engaging part 68a from the engagement part (not shown), allowing the movable member 7 to move relative to the lid body 6.

As shown in FIG. 1, the lid body 6 is also formed with a locking groove 67 near the front end. The lid cover 5 is pivotably attached to the rear end of the lid body 6 and is formed with a lock member 51 near its free end. When the lid cover 5 is closed, then the lock member 51 is deformed and received into the locking groove 67, thereby maintaining the lid cover 5 closed. When the lid cover 5 is closed in this manner, the lid 4 including the lid body 6 and the movable member 7 is covered with the lid cover 5 from the above. On the other hand, when the lid cover 5 is open, the lid 4 is exposed to the upper side.

Figure 8:
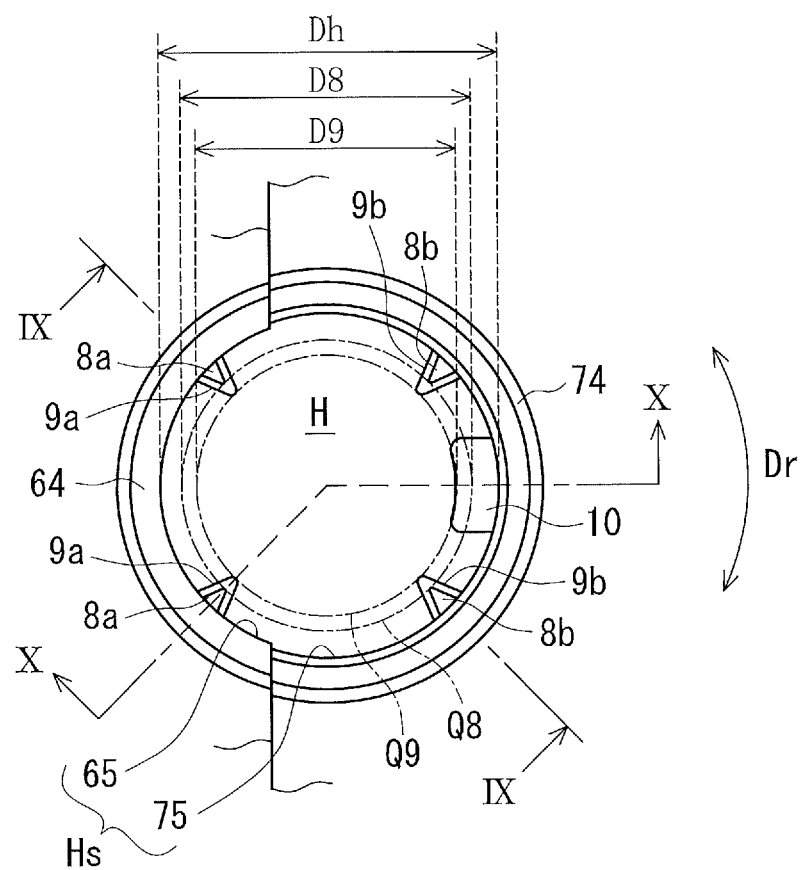
FIG. 8 is a partial plan view showing an insertion opening of the needle disposal container shown in FIG. 1 and peripheral components thereof.

Next, a configuration that enables removal of the needle unit N3 from the injector main body N2 will be described in detail. As shown in FIGS. 8 and 9, the lid 4 is further formed with a first rotation-preventer 8 and a second rotation-preventor 9 on the cylindrical surface Hs of the insertion opening H. The second rotation-preventer 9 is located at a position lower than the first rotation-preventer 8 in the height direction D2 (i.e., at a position closer to the bottom side of the insertion opening H than the first rotation-preventer 8).

The first rotation-preventer 8 includes at least one first protrusion. In this embodiment, however, the first rotation-preventer 8 includes a pair of first protrusions 8a formed on the first surface 65 of the first wall 64 of the lid body 6 with an interval in a circumferential direction Dr of the insertion opening H and a pair of first protrusions 8b formed on the second surface 75 of the second wall 74 of the movable member 7 with an interval in the circumferential direction Dr. The first protrusions 8a and 8b protrude a first amount radially inward of the insertion opening H.

Figure 4:
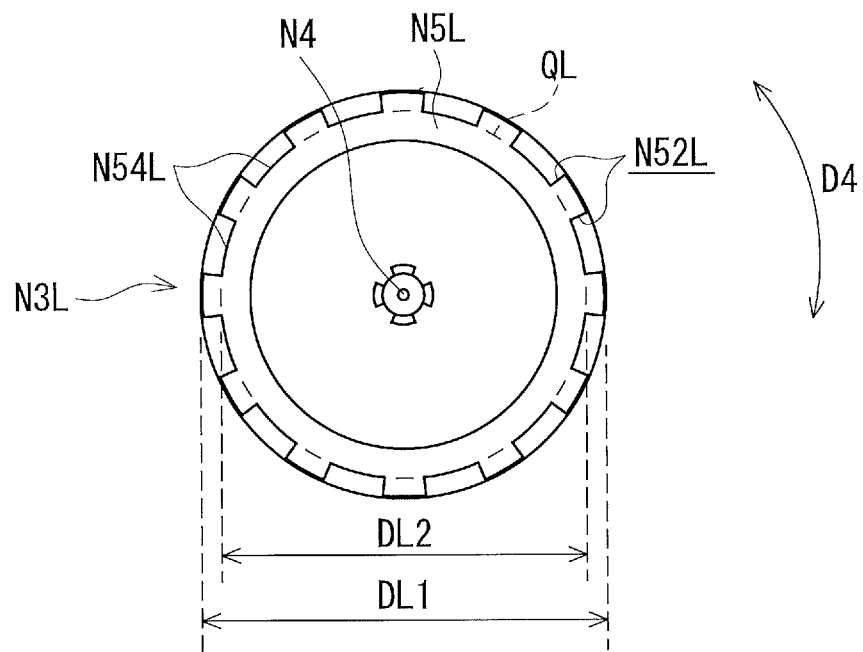
FIG. 4(a) is a bottom view of a first needle unit with a larger diameter.
FIG. 4(b) is a bottom view of a second needle unit with a smaller diameter.
Figure 4:
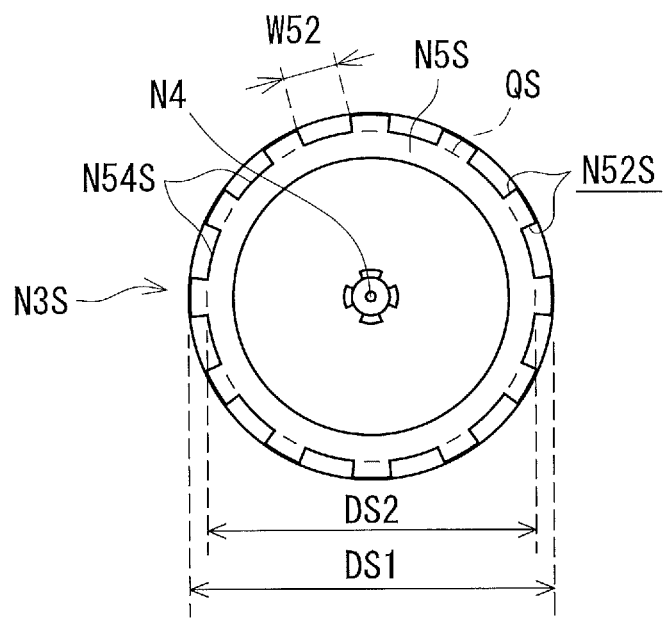

With reference to FIGS. 8 and 4(*a*), a first protrusion imaginary circle Q8 coaxial with the insertion opening H in the narrow state and passing through tip ends of the first protrusions 8a and 8b has a first diameter D8, which is smaller than an outer diameter DL1 of the first needle hub N5L of the first needle unit N3L and larger than a first bottom diameter DL2 of a first hub imaginary circle QL defined by bottom surfaces N54L of the first cutouts N52L of the first needle hub N5L. Also, a diameter Dh of the insertion opening H in the narrow state is set larger than the outer diameter DL1 of the first needle hub N5L, allowing insertion of the first needle unit N3L (first needle hub N5L) into the insertion opening H.

Figure 10:
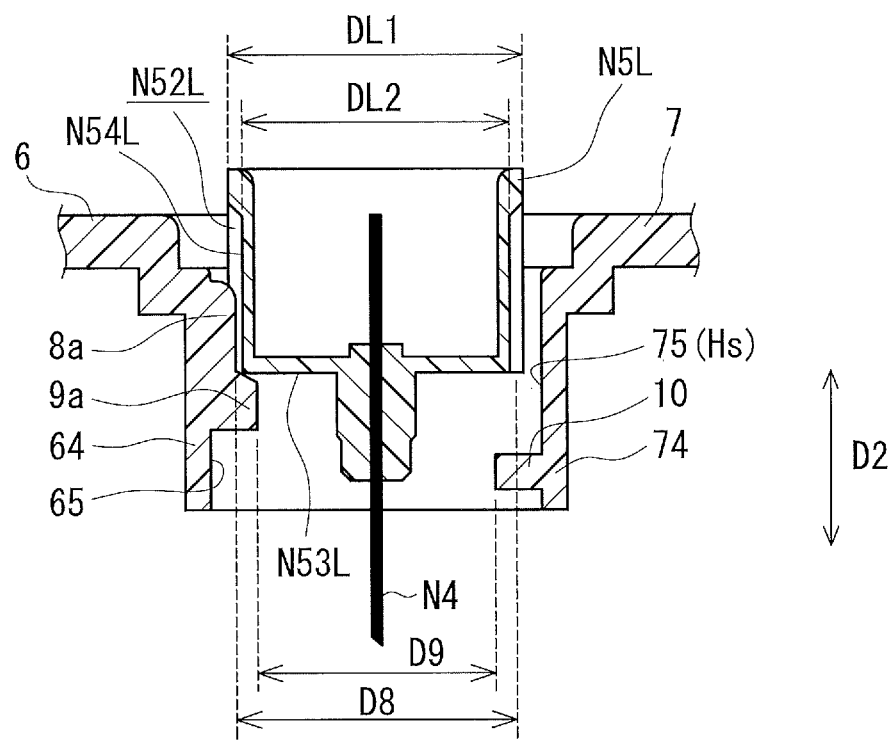
FIG. 10 is a cross-sectional view of the insertion opening taken along a X-X line of FIG. 8 with a first needle hub inserted therein.

With this configuration, when the first needle unit N3L (first needle hub N5L) is inserted into the insertion opening H in the narrow state from the top side, then, as shown in FIG. 10, the first protrusions 8a, 8b are slidingly inserted into four of the first cutouts N52L of the first needle hub N5L through the open distal ends of the first cutouts N52L. As a result, rotation of the needle hub N5L relative to the covering 3 is prevented.

With reference to FIGS. 8 and 9, the second rotation-preventer 9 includes at least one second protrusion. In this embodiment, however, the second rotation-preventer 9 includes a pair of second protrusions 9a formed on the first surface 65 of the first wall 64 of the lid body 6 with an interval in the circumferential direction Dr of the insertion opening H, and a pair of second protrusions 9b formed on the second surface 75 of the second wall 74 of the movable member 7 with an interval in the circumferential direction Dr. The second protrusions 9a and 9b protrude a second amount, which is greater than the first amount, radially inward of the insertion opening H. Also, a thickness of the second protrusion 9a, 9b in the circumferential direction Dr is set greater than a thickness of the first protrusion 8a, 8b such that the second protrusions 9a and 9b have a greater strength.

With reference to FIGS. 8 and 4(*b*), a second protrusion imaginary circle Q9 coaxial with the insertion opening H in the narrow state and passing through tip ends of the second protrusions 9a and 9b has a second diameter D9, which is smaller than an outer diameter DS1 of the second needle hub N5S of the second needle unit N3S and larger than a second bottom diameter DS2 of a second hub imaginary circle QS defined by bottom surfaces N54S of the second cutouts N52S of the second needle hub N5S.

Figure 11:
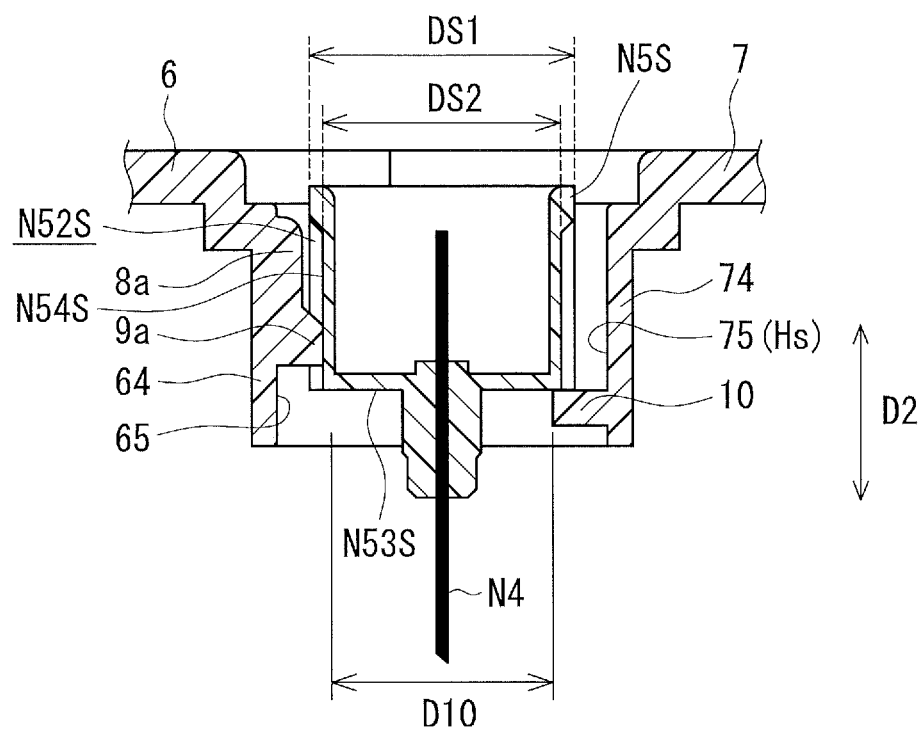
FIG. 11 is a cross-sectional view of the insertion opening shown in FIG. 10 with a second needle hub inserted therein.

With this configuration, when the second needle unit N3S (second needle hub N5S) is inserted into the insertion opening H in the narrow state from the top side, then, as shown in FIG. 11, then the second protrusions 9a and 9b are slidingly inserted into four of the second cutouts N52S of the second needle hub N5S through the open distal ends. As a result, rotation of the second needle hub N5S relative to the covering 3 is prevented.

It should be noted that because the outer diameter DS1 of the second needle hub N5S is smaller than the outer diameter DL1 of the first needle hub N5L, the second needle hub N5S also can be inserted into the insertion opening H in the narrow state from the top side.

Further, with reference to FIGS. 8 and 10, the second diameter D9 of the second protrusion imaginary circle Q9 (FIG. 8) is set smaller than the diameter DL2 of the first hub imaginary circle QL (FIG. 4(*a*)) defined by the bottom surfaces N54L of the first cutouts N52L of the first needle hub N5L. Thus, when the first needle unit N3L is inserted into the insertion opening H in the narrow state from the top side, then the distal end N53L of the first needle hub N5L abuts the second protrusions 9a and 9b as shown in FIG. 10. Thus, the insertion of the first needle hub N5L into the insertion opening H in the narrow state beyond the second protrusions 9a and 9b is prevented.

With reference to FIGS. 8 and 11, the cylindrical surface Hs of the insertion opening H is formed with at least one insert-regulating protrusion 10 at a position lower than the second rotation-preventer 9 (i.e., at a position closer to the bottom side of the insertion opening H than the second rotation-preventer 9). In this embodiment, one insert-preventing protrusion 10 is formed on the second surface 75 of the second wall 74. The insert-preventing protrusion 10 extends along the circumferential direction Dr of the insertion opening H within a predetermined range that preferably has a greater length in the circumferential direction Dr than a width W52 (FIG. 4(*b*)) of the second cutout N52S.

The insert-regulating protrusion 10 extends from the cylindrical surface Hs radially inward of the insertion opening H by a third amount, which is greater than the first amount. Also, a third protrusion imaginary circle passing through a tip end of the insert-preventing protrusion 10 and coaxial with the insertion opening H in the narrow state has a diameter D10, which is smaller than the outer diameter DS1 of the second needle hub N5S of the second needle unit N3S. Thus, when the second needle unit N3S is inserted into the insertion opening H in the narrow state from the top side, the distal end N53S of the second needle hub N5S abuts the insert-preventing protrusion 10. In this manner, insertion of the second needle hub N5S into the insertion opening H in the narrow state beyond the insert-preventing protrusion 10 is prevented.

In this embodiment, the first protrusions 8a and 8b are formed at the same angle positions as the second protrusions 9a and 9b in the circumferential direction Dr of the insertion opening H, i.e., the first protrusions 8a and 8b are aligned with the second protrusions 9a and 9b in the height direction D2. Also, each of the first protrusions 8a and 8b is formed continuous with the corresponding one of the second protrusions 9a and 9b in the height direction D2. Thus, the first needle hub N5L of the first needle unit N3L and the second needle hub N5S of the second needle unit N3S can be inserted into the insertion opening H in the same manner, and there is no need to adjust the orientation of the needle unit N3 depending on whether the needle unit N3 is the first needle unit N3L or the second needle unit N3S when the needle unit N3 is inserted into the insertion opening H.

Next, a method of disposing the first needle unit N3L attached to the injector main body N2L at the needle disposal container 1 will be described. First, the movable member 7 is placed into the hold position. As a result, the movable member 7 is locked at the hold position by the lock part 68, and the insertion opening H is brough into the narrow state.

Then, the first needle hub N5L of the first needle unit N3L is inserted into the insertion opening H from the top side such that the first protrusions 8a and 8b are received into four of the first cutouts N52L of the first needle hub N5L, until the distal end N53L of the first needle hub N5L abuts the second rotation-preventer 9 (the second protrusions 9a and 9b). In this condition, further insertion of the first needle hub N5L into the insertion opening H is prohibited, and the first needle hub N5S is held in the insertion opening H.

Then, the injector main body N2L is rotated in the predetermined detaching direction. Because the first rotation-preventer 8 (the first protrusions 8a and 8b) is placed in the first cutouts N52L of the first needle hub N5L, the first rotation-preventer 8 prevents the first needle hub N5L from rotating relative to the covering 3 while the injector main body N2L is rotated relative to the covering 3. As a result, the injector main body N2L is rotated relative to the first needle unit N3L and detached therefrom.

Thereafter, the movable member 7 is moved to the retract position to bring the insertion opening H into the widened state. As a result, the first needle unit N3L drops into the container body 2 by its own weight. In this manner, a user can remove the first needle unit N3L from the injector main body N2L and dispose the first needle unit N3L into the container body 2 without touching the first needle unit N3L.

Next, a method of disposing the second needle unit N3S attached to the injector main body N2S into the needle disposal container 1 will be described. First, the movable member 7 is placed into the hold position in the same manner as described above.

Then, the second needle hub N5S of the second needle unit N3S is inserted into the insertion opening H in the narrow state from the top side such that the second protrusions 9a, 9b are received into four of the second cutouts N52S of the needle hub N5S, until the distal end N53S of the second needle hub N5S abuts the insert-preventing protrusion 10. In this condition, further insertion of the second needle hub N5S into the insertion opening H is prohibited, and the second needle hub N5S is held in the insertion opening H.

Then, the injector main body N2S is rotated in the detaching direction. Because the second rotation-preventer 9 (the second protrusions 9a and 9b) is placed in the second cutouts N52S of the second needle hub N5S, the second rotation-preventer 9 prevents the second needle hub N5S from rotating relative to the covering 3 while the injector main body N2S is rotated relative to the covering 3. As a result, the injector main body N2S is rotated relative to the second needle unit N3S and detached therefrom.

Then, the movable member 7 is moved to the retract position to bring the insertion opening H into the widened state. As a result, the second needle unit N3S drops into the container body 2 by its own weight. In this manner, a user can remove the second needle unit N3S from the injector main body N2S and dispose the second needle unit N3S into the container body 2 without touching the second needle unit N3S.

Here, the first wall 64 of the lid body 6 preferably has an arc length of less than 180 degrees, and the second wall 74 of the movable member 7 preferably has an arc length of more than 180 degrees. With this configuration, the insertion opening H is widened relatively largely when the movable member 7 is moved to the retract position, letting the needle unit N3 easily drop into the container body 2. In a different embodiment, however, both the first and the second wall 64 and 74 are formed to have an arc length of 180 degrees.

While the invention has been described in detail with reference to the embodiment thereof, it would be apparent to those skilled in the art that various changes and modifications may be made therein without departing from the spirit of the invention.

For example, in the above embodiment, the insert-preventing protrusion 10 is formed on the second wall 74 of the movable member 7. This configuration allows the needle unit N3 to relatively easily drop into the container body 2 when the movable member 7 is moved to the retract position. However, in a different embodiment, the insert-preventing protrusion 10 is formed on the first wall 64 of the lid body 6. Alternatively, the insert-preventing protrusion 10 is formed on either of the first and second walls 64 and 74.

Also, in the above embodiment, each of the first protrusions 8a and 8b is formed continuous with the corresponding one of the second protrusions 9a and 9b. However, the invention is not limited thereto. For example, in another embodiment, the first protrusions 8a are formed discontinuous with the second protrusions 9a, and/or the first protrusions 8b are formed discontinuous with the second protrusions 9b. In an alternative embodiment, one of the first protrusions 8a is formed discontinuous with corresponding one of the second protrusions 9a and the other of the first protrusions 8a is formed continuous with the second protrusion 9a, and/or one of the first protrusions 8b is formed discontinuous with corresponding one of the second protrusions 9b and the other of the first protrusions 8b is formed continuous with the second protrusion 9b.

In the above embodiment, the first rotation-preventer 8 includes the pair of first protrusions 8a formed on the first surface 65 of the lid body 6 and the pair of first protrusions 8b formed on the second surface 75 of the movable member 7. However, in another embodiment, the first rotation-preventer 8 includes one or more than two first protrusions 8a formed on the first surface 65 and/or one or more than two first protrusions 8b formed on the second surface 75. In other words, in order to prevent rotation of the first needle unit N3L, it is sufficient that the first rotation-preventer 8 includes at least one first protrusion 8a or at least one first protrusion 8b.

Further, in the above embodiment, the second rotation-preventer 9 includes the pair of second protrusions 9a formed on the first surface 65 of the lid body 6 and the pair of second protrusions 9b formed on the second surface 75 of the movable member 7. However, in another embodiment, the second rotation-preventer 9 includes one or more than two second protrusions 9a formed on the first surface 65 and/or one or more than two second protrusions 9b formed on the second surface 75. In other words, in order to prevent rotation of the second needle unit N3S, it is sufficient that the second rotation-preventer 9 includes at least one second protrusion 9a or at least one second protrusion 9b.

What is claimed is:

1. A needle disposal container for disposing of a first needle unit having a first needle hub and a second needle unit having a second needle hub with a smaller outer diameter than the first needle hub, comprising:
   a container body having an open top; and
   a covering attached to the container body, wherein:
   the covering includes a lid body that covers the open top of the container body and a movable member attached to the lid body so as to be movable relative to the lid body between a hold position and a retract position in a first direction;
   the lid body is formed with a first wall extending in a second direction perpendicular to the first direction, the first wall having a first surface with a concave-arc cross-section;
   the movable member is formed with a second wall extending in the second direction, the second wall having a second surface with a concave-arc cross-section, the second surface confronting the first surface of the first wall in the first direction;
   the first surface of the first wall and the second surface of the second wall together form a cylindrical surface that defines an insertion opening extending in the second direction, the insertion opening having a top side and a bottom side opposite to the top side in the second direction;
   when the movable member is moved from the hold position to the retract position, then the second wall of the movable member moves away from the first wall of the lid body to widen the insertion opening, bringing the insertion opening into a widened state;
   when the movable member is moved from the retract position to the hold position, then the second wall of the movable member moves toward the first wall of the lid body to narrow the insertion opening, bringing the insertion opening into a narrow state;
   the cylindrical surface is formed with a first rotation-preventer and a second rotation-preventer at a position closer to the bottom side of the insertion opening than the first rotation-preventer;
   the first rotation-preventer prevents rotation of the first needle unit inserted into the insertion opening;
   the second rotation-preventer prevents rotation of the second needle unit inserted into the insertion opening;
   the first rotation-preventer includes at least one first protrusion that protrudes radially inward of the insertion opening from the cylindrical surface;
   the second rotation-preventer includes at least one second protrusion that protrudes radially inward of the insertion opening from the cylindrical surface; and
   a thickness of the at least one second protrusion in a circumferential direction of the insertion opening is greater than a thickness of the at least one first protrusion in the circumferential direction of the insertion opening.

2. The needle disposal container according to claim 1, wherein:
   the at least one first protrusion protrudes radially inward of the insertion opening from the cylindrical surface by a first amount; and
   the at least one second protrusion protrudes radially inward of the insertion opening from the cylindrical surface by a second amount greater than the first amount.

3. The needle disposal container according to claim 2, wherein:
   when the first needle hub is inserted into the insertion opening in the narrow state from the top side, then the first protrusion is inserted into one of first cutouts formed in an outer peripheral surface of the first needle hub; and
   when the second needle hub is inserted into the insertion opening in the narrow state from the top side, then the second protrusion is inserted into one of second cutouts formed in an outer peripheral surface of the second needle hub.

4. The needle disposal container according to claim 3, wherein:
   the first protrusion is aligned with the second protrusion in the second direction;
   a first protrusion imaginary circle coaxial with the insertion opening in the narrow state and passing through a tip end of the first protrusion has a first diameter that is smaller than an outer diameter of the first needle hub and greater than a first bottom diameter of a first hub imaginary circle defined by bottom surfaces of the first cutouts;
   a second protrusion imaginary circle coaxial with the insertion opening in the narrow state and passing through a tip end of the second protrusion has a second diameter that is smaller than an outer diameter of the second needle hub, greater than a second bottom diameter of a second hub imaginary circle defined by bottom surfaces of the second cutouts, and smaller than the first bottom diameter of the first hub imaginary circle; and
   when the first needle hub is inserted into the insertion opening in the narrow state from the top side, then the first needle hub abuts the second protrusion.

5. The needle disposal container according to claim 2, wherein:
   the first protrusion is formed on each of the first surface and the second surface; and
   the second protrusion is formed on each of the first surface and the second surface in continuous with the corresponding first protrusion in the second direction.

6. The needle disposal container according to claim 2, wherein:
   a pair of the first protrusions are formed on the first surface of the first wall with an interval in a circumferential direction of the insertion opening, and another pair of the first protrusions are formed on the second surface of the second wall with an interval in the circumferential direction; and
   a pair of the second protrusions are formed on the first surface of the first wall with an interval in the circumferential direction, and another pair of the second protrusions are formed on the second surface of the second wall with an interval in the circumferential direction.

7. The needle disposal container according to claim 2, wherein the cylindrical surface is formed with at least one insert-regulating protrusion protruding radially inward of the insertion opening at a position closer to the bottom side of the insertion opening than the second protrusion.

8. The needle disposal container according to claim 7, wherein the at least one insert-regulating protrusion protrudes a third amount from the cylindrical surface, the third amount being greater than the first amount.

9. The needle disposal container according to claim 8, wherein the second protrusion abuts the first needle hub when the first needle hub is inserted into the insertion opening in the narrow state; and the insert-regulating protrusion abuts the second needle hub when the second needle hub is inserted into the insertion opening in the narrow state.

10. The needle disposal container according to claim 1, wherein:
the cylindrical surface is formed with at least one insert-preventing protrusion at a position closer to the bottom side of the insertion opening than the second rotation-preventer; and
when the second needle hub is inserted into the insertion opening in the narrow state from the top side, the at least one insert-preventing protrusion abuts the second needle hub.

11. A needle disposal container for disposing of a first needle unit having a first needle hub and a second needle unit having a second needle hub with a smaller outer diameter than the first needle hub, comprising:
a container body having an open top; and
a covering attached to the container body, wherein:
the covering includes a lid body that covers the open top of the container body and a movable member attached to the lid body so as to be movable relative to the lid body between a hold position and a retract position in a first direction;
the lid body is formed with a first wall extending in a second direction perpendicular to the first direction, the first wall having a first surface with a concave-arc cross-section;
the movable member is formed with a second wall extending in the second direction, the second wall having a second surface with a concave-arc cross-section, the second surface confronting the first surface of the first wall in the first direction;
the first surface of the first wall and the second surface of the second wall together form a cylindrical surface that defines an insertion opening extending in the second direction, the insertion opening having a top side and a bottom side opposite to the top side in the second direction;
when the movable member is moved from the hold position to the retract position, then the second wall of the movable member moves away from the first wall of the lid body to widen the insertion opening, bringing the insertion opening into a widened state;
when the movable member is moved from the retract position to the hold position, then the second wall of the movable member moves toward the first wall of the lid body to narrow the insertion opening, bringing the insertion opening into a narrow state;
the cylindrical surface is formed with a first rotation-preventer and a second rotation-preventer at a position closer to the bottom side of the insertion opening than the first rotation-preventer;
the first rotation-preventer prevents rotation of the first needle unit inserted into the insertion opening;
the second rotation-preventer prevents rotation of the second needle unit inserted into the insertion opening;
the first rotation-preventer includes at least one first protrusion that protrudes radially inward of the insertion opening from the cylindrical surface by a first amount;
the second rotation-preventer includes at least one second protrusion that protrudes radially inward of the insertion opening from the cylindrical surface by a second amount greater than the first amount;
when the first needle hub is inserted into the insertion opening in the narrow state from the top side, then the first protrusion is inserted into one of first cutouts formed in an outer peripheral surface of the first needle hub;
when the second needle hub is inserted into the insertion opening in the narrow state from the top side, then the second protrusion is inserted into one of second cutouts formed in an outer peripheral surface of the second needle hub;
the first protrusion is aligned with the second protrusion in the second direction;
a first protrusion imaginary circle coaxial with the insertion opening in the narrow state and passing through a tip end of the first protrusion has a first diameter that is smaller than an outer diameter of the first needle hub and greater than a first bottom diameter of a first hub imaginary circle defined by bottom surfaces of the first cutouts;
a second protrusion imaginary circle coaxial with the insertion opening in the narrow state and passing through a tip end of the second protrusion has a second diameter that is smaller than an outer diameter of the second needle hub, greater than a second bottom diameter of a second hub imaginary circle defined by bottom surfaces of the second cutouts, and smaller than the first bottom diameter of the first hub imaginary circle; and
when the first needle hub is inserted into the insertion opening in the narrow state from the top side, then the first needle hub abuts the second protrusion.

12. A needle disposal container for disposing of a first needle unit having a first needle hub and a second needle unit having a second needle hub with a smaller outer diameter than the first needle hub, comprising:
a container body having an open top; and
a covering attached to the container body, wherein:
the covering includes a lid body that covers the open top of the container body and a movable member attached to the lid body so as to be movable relative to the lid body between a hold position and a retract position in a first direction;
the lid body is formed with a first wall extending in a second direction perpendicular to the first direction, the first wall having a first surface with a concave-arc cross-section;
the movable member is formed with a second wall extending in the second direction, the second wall having a second surface with a concave-arc cross-section, the second surface confronting the first surface of the first wall in the first direction;
the first surface of the first wall and the second surface of the second wall together form a cylindrical surface that defines an insertion opening extending in the second direction, the insertion opening having a top side and a bottom side opposite to the top side in the second direction;
when the movable member is moved from the hold position to the retract position, then the second wall of the movable member moves away from the first wall of the lid body to widen the insertion opening, bringing the insertion opening into a widened state;
when the movable member is moved from the retract position to the hold position, then the second wall of the movable member moves toward the first wall of the lid body to narrow the insertion opening, bringing the insertion opening into a narrow state;

the cylindrical surface is formed with a first rotation-preventer and a second rotation-preventer at a position closer to the bottom side of the insertion opening than the first rotation-preventer;
the first rotation-preventer prevents rotation of the first needle unit inserted into the insertion opening;
the second rotation-preventer prevents rotation of the second needle unit inserted into the insertion opening;
the first rotation-preventer includes at least one first protrusion that protrudes radially inward of the insertion opening from the cylindrical surface by a first amount;
the second rotation-preventer includes at least one second protrusion that protrudes radially inward of the insertion opening from the cylindrical surface by a second amount greater than the first amount;
a pair of the first protrusions are formed on the first surface of the first wall with an interval in a circumferential direction of the insertion opening, and another pair of the first protrusions are formed on the second surface of the second wall with an interval in the circumferential direction; and
a pair of the second protrusions are formed on the first surface of the first wall with an interval in the circumferential direction, and another pair of the second protrusions are formed on the second surface of the second wall with an interval in the circumferential direction.

* * * * *